United States Patent [19]

de Groot

[11] Patent Number: 5,056,529

[45] Date of Patent: Oct. 15, 1991

[54] APPARATUS AND METHOD FOR PERFORMING A TRANSBRONCHEAL BIOPSY

[76] Inventor: William J. de Groot, No. 1 Cedar Lawn South, Galveston, Tex. 77550

[21] Appl. No.: 503,758

[22] Filed: Apr. 3, 1990

[51] Int. Cl.$^5$ .............................................. A61B 10/00
[52] U.S. Cl. ..................................... 128/754; 128/756; 606/170; 606/172
[58] Field of Search ............... 128/754, 753, 751, 744, 128/756, 757; 604/272, 280, 21, 22, 51, 164, 264; 606/170, 171, 172

[56] References Cited

U.S. PATENT DOCUMENTS

| 4,617,940 | 10/1986 | Wang | 128/753 |
| 4,702,260 | 10/1987 | Wang | 128/753 |
| 4,766,907 | 8/1988 | de Groot et al. | 128/754 |
| 4,880,015 | 11/1989 | Nierman | 128/751 |
| 4,893,635 | 1/1990 | de Groot et al. | 128/754 |

FOREIGN PATENT DOCUMENTS 1217374  3/1986  U.S.S.R. ............................. 606/172

Primary Examiner—Kyle L. Howell
Assistant Examiner—Scott Akers
Attorney, Agent, or Firm—Brady O'Boyle & Gates

[57] ABSTRACT

Apparatus and a method for performing a transbroncheal biopsy wherein a bronchoscope is inserted into the lower broncheal tree of a patient, and a manipulator is inserted through the bronchoscope to obtain a specimen cell from the lung. An activator device is connected to the manipulator to move the manipulator through a sequence of steps to obtain the specimen.

4 Claims, 4 Drawing Sheets

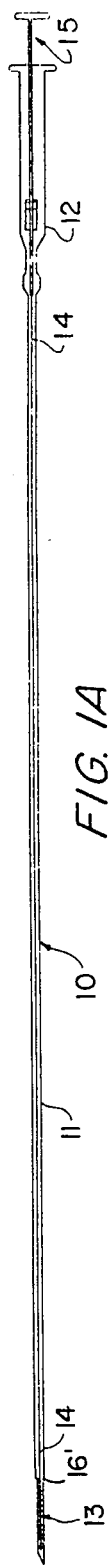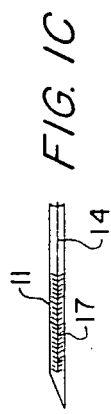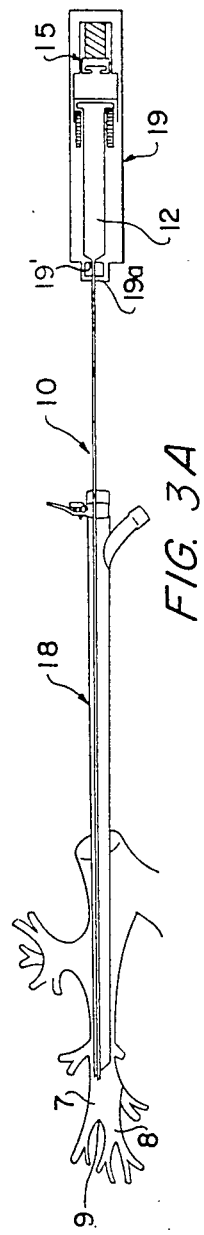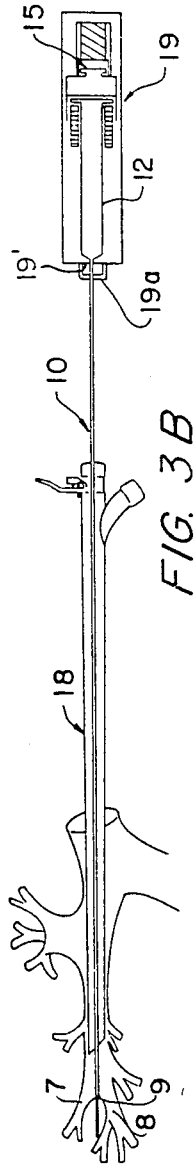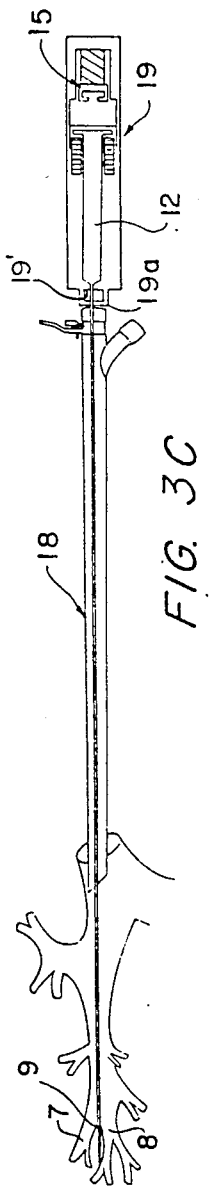

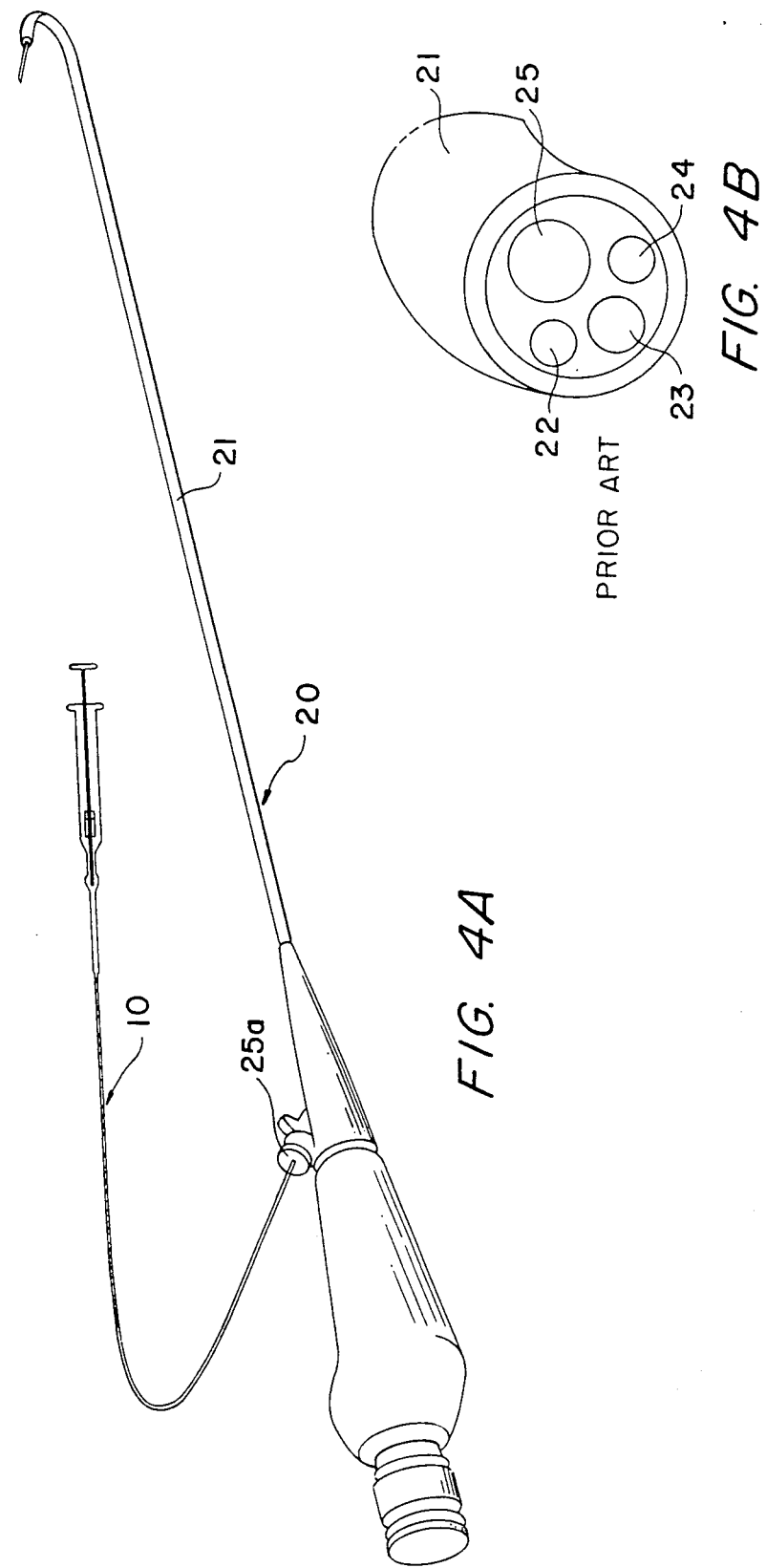

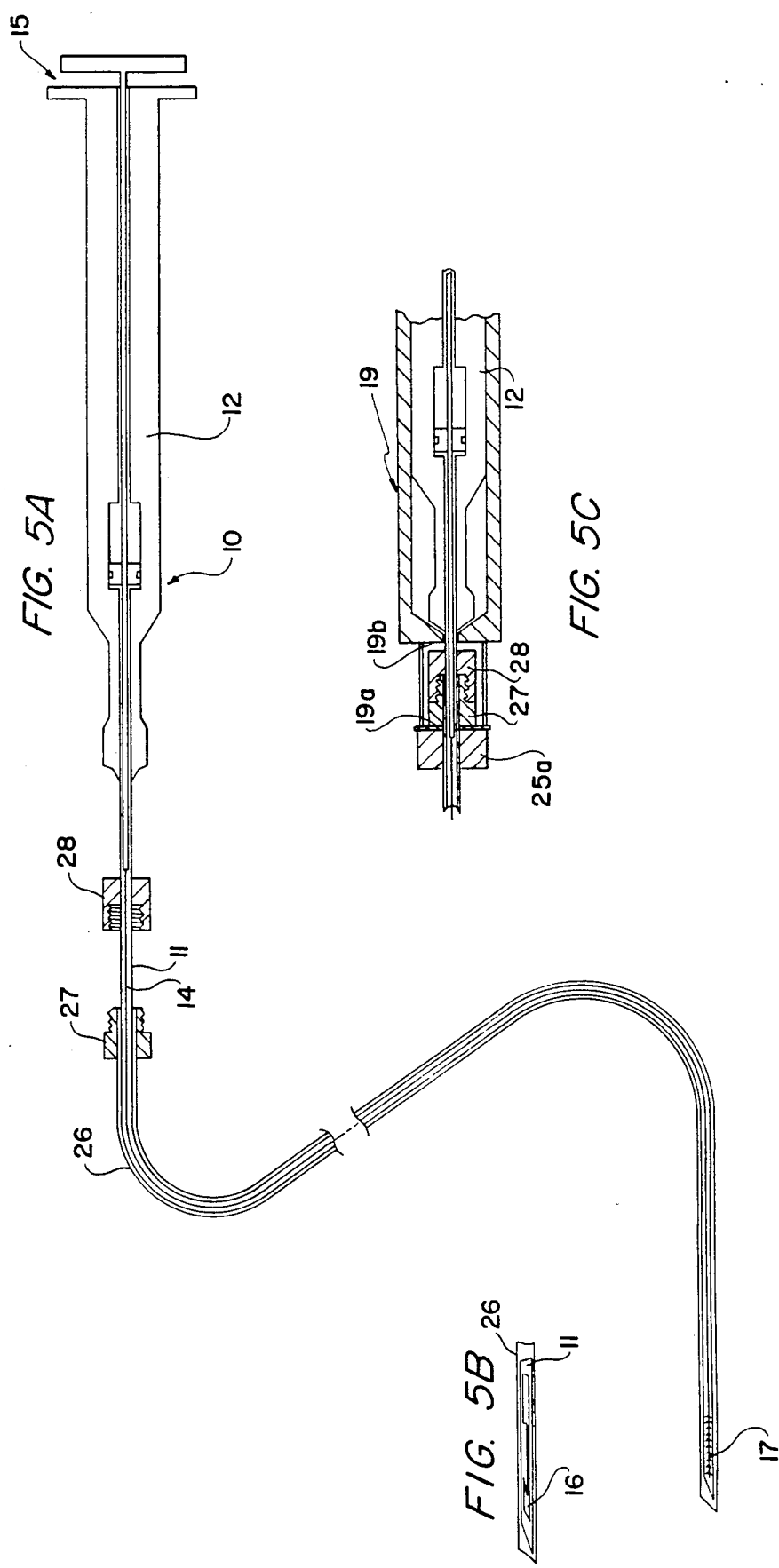

5,056,529

APPARATUS AND METHOD FOR PERFORMING A TRANSBRONCHEAL BIOPSY

BACKGROUND OF THE INVENTION

In my U.S. Pat. No. 4,766,907 dated Aug. 30, 1988, and U.S. Pat. No. 4,893,635 dated Jan. 16, 1990, apparatus and a method for performing a percutaneous biopsy are disclosed. The apparatus includes a manipulator which comprises a long thin cannula needle having one end connected to a syringe cylinder. A cell retrieving instrument is slidably mounted in the needle, and one end of the cell retrieving instrument is connected to the syringe plunger. By this construction and arrangement, cells are obtained from the patient's lung by inserting the needle, with the cell retrieving instrument wholly contained therein, inwardly through the patient's chest into the lung. The cell retrieving instrument is held fixed while the needle is slid outwardly relative thereto, to thereby expose the cell retrieving instrument within the patient's lung. The needle is then held fixed while the cell retrieving instrument is slid outwardly into the needle. The needle, the wholly contained instrument, and retrieved cell are then removed from the patient's lung.

The above-mentioned patents also disclose an activator device to which the manipulator is detachably connected to facilitate the direction, sequence, and distance of movement of the needle and associated cell retrieving instrument.

While the apparatus and method disclosed in my aforementioned patents were developed to meet a growing and unaddressed need for a simple, safe and effective non-surgical means to retrieve lung cells or tissue for diagnostic purposes and were directed to performing a percutaneous lung biopsy, there are times and circumstances when it is preferable to obtain a cytologic or histologic biopsy of the lung parenchyma using a transbroncheal method rather than a percutaneous method. The main advantage of the transbroncheal method over the percutaneous method, as they are both currently practiced, is the substantially lower incidence of pneumothorax; that is, allowing air to enter the pleural space, resulting in a collapsed lung.

Transbroncheal lung biopsy is presently performed almost exclusively with a flexible fiberoptic bronchoscope, wherein a small brush or biopsy forceps is passed through a "suction/forceps" channel provided in the bronchoscope, and then forced through a very small peripheral bronchus into the substance of the lung. This is all done using a fluoroscope to guide the distance the biopsy device is forced into the lung.

While conventional transbroncheal lung biopsys have been satisfactory, they have been characterized by certain disadvantages. For instance, a fluoroscope is required, thereby substantially increasing the expense of the procedure. Furthermore, the biopsy specimens are not always optimum. At times, especially when a small brush is employed, the biopsy instrument fails to enter the lung, whereby the specimen consists of cells or tissue harvested from the airway rather than from the lung. When biopsy forceps are employed, the instrument tends to crush the specimen, thereby distorting the histology to a variable degree.

SUMMARY OF THE INVENTIONS

To overcome the disadvantages experienced, when performing conventional transbroncheal lung biopsys, the apparatus and method of the present invention has been devised wherein the manipulator and activator device disclosed in my aforementioned patents, the disclosures of which are incorporated herein by reference, are operatively connected to a bronchoscope which can be either a rigid bronchoscope inserted through the mouth of the patient and passed into the lower broncheal tree, or a flexible fiberoptic bronchoscope which can be passed through the nose or mouth of the patient and further into the lower broncheal tree to the subsegmental bronchi. The manipulator is passed through the selected bronchoscope and the distal needle tip of the manipulator is then forcibly passed through the bronchial wall at any intrapulmonary bronchial bifurcation under direct visual observation through the bronchoscope, thus eliminating the need for fluoroscopic visualization. The needle shaft then lies within the lung parenchyma, the depth of penetration being limited by a shoulder on the needle wall proximal to the needle tip. Actuation of the activator then causes retraction of the needle a predetermined distance exposing the cell or tissue retrieving element. The cell or tissue retrieving element is then retracted into the needle, after which the manipulator is manually removed from its point of insertion, and from the bronchoscope.

The method of positively positioning the needle within the lung parenchyma and the use of the tissue retrieving device, disclosed in my aforementioned patents, substantially increases the probability of harvesting lung tissue and obtaining a tissue biopsy free of artifact.

BRIEF DESCRIPTION OF THE DRAWINGS

FIG. 1A is a side elevational view of a biopsy device or manipulator of the type disclosed in my U.S. Pat. Nos. 4,766,907 and 4,893,635;

FIG. 1B is a fragmentary, side elevational view illustrating a Cope needle as the tissue retrieving instrument;

FIG. 1C is a fragmentary, side elevational view showing a brush as the cell retrieving instrument;

FIG. 3A is a side elevational view of the biopsy device or manipulator of FIG. 1A and associated activator device used with the rigid bronchoscope of FIG. 2A;

FIG. 3B is a side elevational view similar to FIG. 3A but showing the needle and enclosed cell retrieving instrument pushed forwardly through the open end of the rigid bronchoscope, through the bronchus and into the lung;

FIG. 3C is a side elevational view similar to FIGS. 3A and 3B showing the bronchoscope retracted to provide a fixed platform upon which to rest the adjustable flange of the biopsy activator device, and also showing the needle retracted to expose the cell retrieving instrument to the cells within the lung;

FIG. 4A is a perspective view of a flexible fiberoptic bronchoscope employing the biopsy device of FIG. 1A;

FIG. 4B is a cross-sectional view of the distal end portion of the flexible bronchoscope showing light and optical bundles and a suction/biopsy channel;

FIG. 5A is a fragmentary, side elevational view of the biopsy device or manipulator of FIG. 1A having a long needle enclosed by a retractable protective sheath and adapted to be inserted into the suction/biopsy channel of the flexible bronchoscope shown in FIG. 4A:

FIG. 5B is a fragmentary, side elevational view of the end of the sheathed long needle of FIG. 5A having a Cope needle as the tissue retrieving instrument: and FIG. 5C is a fragmentary, side elevational view of the biopsy device or manipulator of FIG. 5A and associated activator device used with the flexible fiberoptic bronchoscope of FIG. 4A.

DESCRIPTION OF THE PREFERRED EMBODIMENTS

Figure 2A:
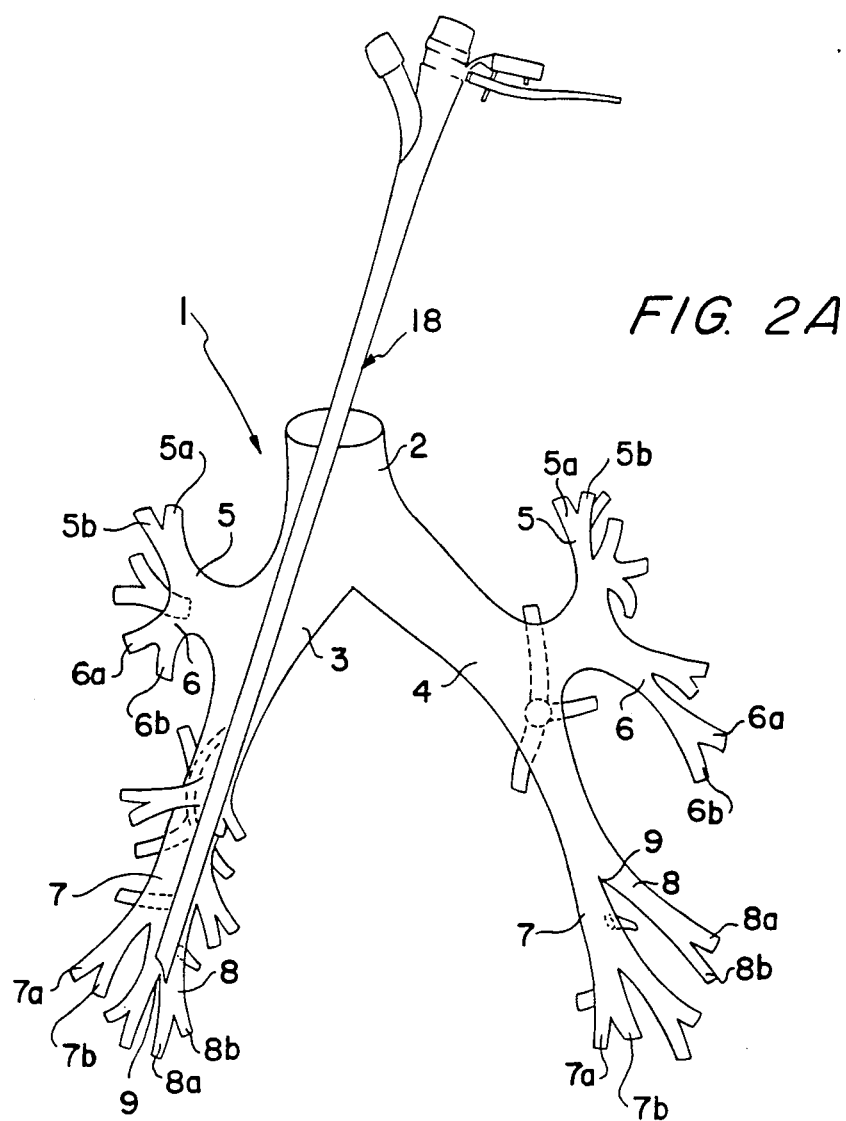
FIG. 2A is a diagrammatic view of a tracheobroncheal tree showing a rigid bronchoscope inserted to the beginning of the segmental bronchi of the lower lobes of the broncheal tree.
Figure 2B:
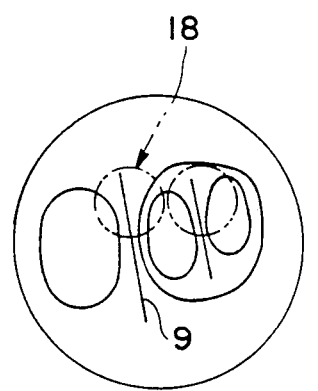
FIGS. 2B and 2C are diagrammatic plan views of several bronchial bifurcations of the right and left lung as seen through a bronchoscope showing preferred biopsy needle puncture sites in the broncheal tree of FIG. 2A.
Figure 2C:
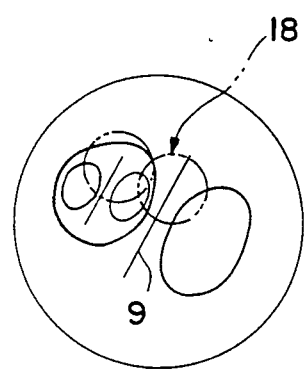

Referring to the drawings and more particularly to FIG. 2A, a diagrammatic view of the broncheal tree 1 is shown which includes a trachea portion 2 communicating with a right main bronchus 3 and a left main bronchus 4, which in turn communicate with segmental intrapulmonary airways such as 5, 6, 7 and 8 which are surrounded by lung tissue. The segmental intrapulmonary airways are further divided into subsegmental airways 5a, 5b; 6a, 6b; 7a, 7b; and 8a, 8b which are also surrounded by lung tissue. A bifurcation 9, for example, is formed where a larger broncheal tube divides into smaller bronchi and the ridge formed at the point of broncheal bifurcation is known as the "carina". Several carinae 9 of the right and left lower lung, viewed respectively from the right and left main bronchi 3 and 4, are shown in FIGS. 2B and 2C.

When a transbroncheal biopsy is conducted, a needle with a slidably mounted cell retrieving instrument housed within penetrates the wall of an intrapulmonary bronchus in proximity to one of several carinae. Example areas of preferred needle penetration are depicted within the circular broken lines shown in FIGS. 2B and 2C.

FIG. 1A illustrates a cell or tissue retrieving instrument 10 referred to as a "manipulator", and is of the type disclosed in my aforementioned U.S. patents, and includes a long thin cannula needle 11 having one end connected to a syringe cylinder 12. A cell retrieving instrument 13 is slidably mounted and wholly contained within the needle 11 and is connected by a wire 14 to the syringe plunger 15. The wall thickness of the needle is reduced at the distal end portion thereof to thereby form a shoulder 16' which will limit the depth of needle penetration.

As will be seen in FIGS. 1B and 1C, the tissue or cell retrieving instrument 13 may be either a Cope needle 16 or a brush 17.

FIGS. 2A and 3A to 3C illustrate the method of performing a transbroncheal biopsy employing a conventional rigid bronchoscope 18 which is essentially a polished stainless steel tube approximately 35 cm long and 6-8 mm in diameter. The tube 18 is inserted through the mouth of the patient and into the lower broncheal tree as shown in FIG. 2A. Because of its size, the end of the rigid bronchoscope 18 cannot be passed any further than the beginning of the segmental bronchi 7, 8 of the lower lobes. After the rigid bronchoscope has been so positioned, the manipulator 10 is inserted into the bronchoscope as shown in FIG. 3A, with the cylinder 12 and housed or plunger 15 being connected to the actuator device 19. The manipulator needle 11 and wholly contained cell retrieving instrument 13 are pushed further through the bronchoscope and through the bifurcation 9 of the bronchus and into the lung, as shown in FIG. 3B. The bronchoscope 18 is then retracted as shown in FIG. 3C until the end thereof abuts the adjustable flange 19a on the actuator device 19, whereby the end of the bronchoscope provides a fixed platform against which the activator 19 rests during the actuation thereof. Upon actuation of the activator device, the cell retrieving instrument 13 is held fixed while the needle 11 is retracted to expose the cell retrieving instrument 13 within the patient's lung: the needle 11 is then held fixed while the cell retrieving instrument 13 is then retracted into the needle 11. The needle 11, the wholly contained instrument 13 and retrieved cell are then removed from the patient's lung and from the bronchoscope 18.

While the rigid bronchoscope 18 limits biopsys to the segmental bronchi 7, 8; if it is desired to obtain a biopsy further into the lower broncheal tree in the region of the subsegmental bronchi 7a, 7b, a conventional flexible fiberoptic bronchoscope 20, as shown in FIGS. 4A and 4B, is employed. The flexible bronchoscope is a tubular member 21 having a length of 80-85 cm and an outside diameter of 6 to 6.5 mm. A plurality of longitudinally extending tubular channels 22, 23, 24 and 25 are provided in the tubular member for accommodating fiberlight bundles, fiberoptic bundles and the biopsy device 10.

The manipulator 10 to be used with the flexible bronchoscope 20 is somewhat modified as shown in FIGS. 5A and 5B. The major portion of the needle 11 and wire 14 are flexible to match the flexibility of the bronchoscope 20 through which they must pass. In order to protect the interior wall of the channel 25 from damage by the needle 11 passing therethrough, the needle 11 is surrounded by a plastic sheath 26 having an unretracted length greater than the length of the needle as shown in FIG. 5B. A threaded nut 27 is secured to the proximate end of the sheath 26 and adapted to be manually threaded into a collar 28 fixedly mounted on the proximate end portion of the needle 11. When the nut 27 is threaded into the collar 28, the sheath 26 is retracted to a position whereby the needle 11 and wholly contained cell retrieving instrument 13 extend beyond the open end of the sheath 26.

In use, the flexible bronchoscope 20 is passed through the nose or mouth of the patient and into the lung to the subsegmental bronchi. The sheathed needle 11 is then inserted into the entrant portion 25a of the flexible bronchoscope 20, through channel 25 to the open end of the bronchoscope. The sheath 26 is then retracted by securing the nut 27 to the collar 28, as shown in FIG. 5C, to thereby expose the distal end of the needle 11 to the interior of the lung. The cylinder 12 and plunger 15 are then positioned in the activator device 19, as shown in FIGS. 3A to 3C with the assembled nut 27 and collar 28 positioned between the activator flange 19a and the activator housing end wall 19b the activator flange 19a being semi-circular and having a slot formed therein, as shown in my aforementioned patents, whereby the sheath 26 extends through the slot while the nut 27 and collar 28 are positioned between the activator flange 19a and the activator housing end wall 19b. The flange 19a is positioned to abut the bronchoscope entrant portion 25a to thereby provide a fixed platform for the activator device 19 which is then actuated to move the manipulator 10 in the sequence to obtain the biopsy specimen as described hereinabove with regard to the transbroncheal biopsy performed with the rigid bronchoscope.

It is to be understood that the forms of the invention herewith shown and described are to be taken as preferred examples of the same, and that various changes in the shape, size and arrangement of parts may be resorted to, without departing from the spirit of the invention or scope of the subjoined claims.

I claim:

1. Apparatus for obtaining cells in performing a transbroncheal lung biopsy comprising, a rigid bronchoscope having a proximate end and a distal end adapted to be inserted into the lower broncheal tree of a patient, a manipulator inserted into the proximate end of said bronchoscope, said manipulator including a relatively long thin needle, a shoulder provided on the wall of said needle in proximity to the top thereof, a cell retrieving instrument slidably mounted in said needle, a syringe assemble connected to said needle and said cell retrieving instrument, said syringe assembly including a cylinder portion connected to one end of said needle, and a plunger portion slidably mounted in said cylinder portion, said cell retrieving instrument being connected to said plunger portion, whereby the needle and cell retrieving instrument can be slid relative to each other, and an activator device, having an adjustable flange portion, connected to the cylinder portion and the plunger portion of the manipulator said adjustable flange engaging with the proximate end of said bronchoscope to thereby provide a fixed platform against which the activator device rests during the actuation thereof, whereby a specimen cell can be obtained by inserting the bronchoscope into the lower broncheal tree of the patient, inserting the manipulator through the bronchoscope and into the lung parenchyma of the patient, the depth of penetration being limited by the needle shoulder, retracting the bronchoscope until the end thereof abuts the adjustable flange portion on the activator device, actuating the activator device to move the manipulator through a sequence wherein the cell retrieving instrument is held fixed while the needle is retracted to expose the cell retrieving instrument within the patient's lung, the needle then being held fixed while the cell retrieving instrument is then retracted into the needle.

2. Apparatus for obtaining cells in performing a transbronchial lung biopsy comprising a flexible bronchoscope adapted to be inserted into the lower broncheal tree of a patient, an entrant portion communicating with a longitudinally extending biopsy channel provided in said flexible bronchoscope, a manipulator inserted into said channel, said manipulator including a relatively long thin needle having a distal end portion and a proximate end portion, a cell retrieving instrument slidably mounted in said needle, a syringe assembly connected to the proximate end portion of said needle and said cell retrieving instrument, said syringe assembly including a cylinder portion connected to the proximate end of said needle, and a plunger portion slidably mounted in said cylinder portion, said cell retrieving instrument being connected to said plunger portion, whereby the needle and cell retrieving instrument can be slid relative to each other, a retractable sheath surrounding said needle, said sheath having a distal end portion in proximity to the distal end portion of said needle and a proximate end portion, said sheath having an unretracted length greater than the length of the needle, fastener means secured to the proximate end portion of said sheath, cooperating fastener means mounted on the proximate end portion of said needle, whereby the sheath is moved to the retracted position and the fastener means are interconnected, to thereby extend the distal end of the needle and wholly contained cell retrieving instrument beyond the open end of the sheath, and an activator device, having an adjustable flange portion, connected to the cylinder portion and the plunger portion of the manipulator, said adjustable flange portion engageable with said bronchoscope entrant portion, to thereby provide a fixed platform against which the activator device rests during the actuation thereof, whereby the manipulator is moved through a sequence wherein the cell retrieving instrument is held fixed while the needle is retracted to expose the cell retrieving instrument within the patient's lung, the needle then being held fixed while the cell retrieving instrument is then retracted into the needle.

3. Apparatus according to claim 2, wherein the fastener means comprises a threaded nut secured to the proximate end of the sheath, and said cooperating fastener means comprises a collar fixedly connected to the proximate end portion of said needle.

4. A method for obtaining cells in lung tissue while performing a transbronchial biopsy on a patient employing a bronchoscope, a relatively long thin needle having a shoulder portion provided on the wall thereof in proximity to the needle tip, and a cell retrieving instrument slidably mounted in the needle comprising the steps of:

a) inserting the bronchoscope into the lower broncheal tree of the patient;

b) inserting the needle, with the cell retrieving instrument wholly contained therein, through the bronchoscope and into the patient's broncheal wall at an intrapulmonary broncheal bifurcation under direct visual observation through the bronchoscope;

c) limiting the depth of penetration of the needle within the lung parenchyma by engagement of the lung parenchyma and the shoulder portion of the needle;

d) retracting the bronchoscope;

e) maintaining the cell retrieving instrument fixed while sliding the needle outwardly relative thereto, to thereby expose the cell retrieving instrument within the patient's lung;

f) maintaining the needle fixed while sliding the cell retrieving instrument in an outward direction into the needle; and g) removing the needle, the wholly contained instrument and retrieved cell from the patient's lung and outwardly from the bronchoscope.

* * * * *